(12) United States Patent
Hoeppner

(10) Patent No.: US 8,142,342 B2
(45) Date of Patent: Mar. 27, 2012

(54) BLOOD SEPARATING DEVICE

(75) Inventor: Jacy C. Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 13/223,751

(22) Filed: Sep. 1, 2011

(65) Prior Publication Data

US 2011/0319249 A1 Dec. 29, 2011

Related U.S. Application Data

(62) Division of application No. 12/126,028, filed on May 23, 2008, now Pat. No. 8,012,077.

(51) Int. Cl.
*B04B 1/02* (2006.01)
*B04B 7/08* (2006.01)

(52) U.S. Cl. .................. 494/43; 494/1; 494/48; 494/63; 210/782

(58) Field of Classification Search .................. 494/1–4, 494/43, 47, 48, 63; 210/740, 782
See application file for complete search history.

(56) References Cited

U.S. PATENT DOCUMENTS

2004/0251217 A1* 12/2004 Leach et al. .................... 494/37
* cited by examiner

*Primary Examiner* — Walter D Griffin
*Assistant Examiner* — Timothy Cleveland
(74) *Attorney, Agent, or Firm* — Harness, Dickey

(57) ABSTRACT

A device for separating components of a composition according to density. The device includes a rotatable chamber and a plurality of buoys. The rotatable chamber has an axis of rotation. The plurality of buoys are positioned within the rotatable chamber and about the axis of rotation. The buoys are radially movable between an expanded position in which the buoys are at a first location relative to the axis of rotation and a contracted position in which the buoys are at a second location relative to the axis of rotation. The first location is further from the axis of rotation than the second location is. The buoys are movable in response to force generated during rotation of the rotatable chamber.

22 Claims, 9 Drawing Sheets

BLOOD SEPARATING DEVICE

CROSS-REFERENCE TO RELATED APPLICATIONS

This application is a divisional of U.S. patent application Ser. No. 12/126,028 filed on May 23, 2008. The entire disclosure of the above application is incorporated herein by reference.

FIELD

The present disclosure relates to devices and methods for separating blood into its different fractions or parts.

BACKGROUND

The statements in this section merely provide background information related to the present disclosure and may not constitute prior art.

Whole blood includes a variety of different fractions or parts. For example, human whole blood includes platelet rich plasma (PRP), platelet poor plasma (PPP), red blood cells (RBCS), and white blood cells (WBCs). These different blood fractions have a variety of clinical and experimental uses. Thus, there is a need for devices and methods that separate and isolate the different fractions of whole blood, as well as the different components of most any other multi-component composition.

SUMMARY

The present teachings provide for a device for separating components of a composition according to density. The device includes a rotatable chamber and a plurality of buoys. The rotatable chamber has an axis of rotation. The plurality of buoys are positioned within the rotatable chamber and about the axis of rotation. The buoys are radially movable between an expanded position in which the buoys are at a first location relative to the axis of rotation and a contracted position in which the buoys are at a second location relative to the axis of rotation. The first location is further from the axis of rotation than the second location is. The buoys are movable in response to force generated during rotation of the rotatable chamber.

The present teachings further provide for a blood component separation device that includes a rotatable chamber, a plurality of buoys, a first capture area, a second capture area, and a third capture area. The rotatable chamber has an axis of rotation, an inner wall surface, and a floor that is inclined from the axis of rotation to the inner wall surface. The plurality of buoys surround the axis of rotation and are slidable along the floor so as to move radially between an expanded position in which the buoys are distal to the axis of rotation when the chamber is rotating and a contracted position in which the buoys are proximate to the axis of rotation when the chamber is stationary. The buoys have a density that is proximate to the density of platelet rich plasma. The first capture area is between an inner surface of the buoys in the contracted position and the axis of rotation. The first capture area captures platelet poor plasma after blood is spun in the separation device. The second capture area is between an outer surface of the buoys in the contracted position and the inner wall surface of the rotatable chamber. The second capture area captures red blood cells after blood is spun in the separation device. The third capture area is between the first capture area and the second capture area. The third capture area captures platelet rich plasma after blood is spun in the separation device.

The present teachings also provide for a method for separating whole blood into different components. The method includes the following: inserting whole blood into a rotatable chamber of a blood separation device having an axis of rotation and an inner wall surface; rotating the chamber for a sufficient period of time such that components of the whole blood separate according to density; and stopping rotation of the chamber such that the plurality of buoys move from an expanded position in which the buoys are distal to the axis of rotation to a contracted position in which the buoys are proximal to the axis of rotation to isolate red flood cells of the blood between the buoys and the inner wall surface, to isolate platelet poor plasma between the buoys and the axis of rotation, and to isolate platelet rich plasma at a common distance from the axis of rotation as the buoys.

The present teachings provide for a blood component separation device. The device includes a rotatable chamber having an axis of rotation, an inner wall surface, and a floor that is inclined from the axis of rotation to the inner wall surface. The device further includes a plurality of buoys positioned within the rotatable chamber and surrounding the axis of rotation. Each of the buoys have a density that permits the buoys to settle at an interface between red blood cells and a platelet rich plasma buffy coat. Each of the buoys are slidable along the floor so as to move radially between an expanded position in which the buoys are distal to the axis of rotation when the chamber is rotating and a contracted position in which the buoys are proximate to the axis of rotation when the chamber is stationary. Each of the buoys include an arcuate outer surface, an arcuate inner surface, a substantially linear side surface, and a collection trough between the outer surface and the inner surface. The device further includes a collection bowl, a fluid line, a collection basin, a valve, a first capture area, a second capture area, and a third capture area. The collection bowl is at the axis of rotation. The fluid line extends between the collection trough and the collection bowl. The collection basin is attached to a base of the rotatable chamber. The valve is positioned to regulate passage of material between the rotatable chamber and the collection basin. The first capture area is between the inner surfaces of the buoys in the contracted position and the axis of rotation. The first capture area captures platelet poor plasma after blood is spun in the separation device. The second capture area is between the outer surfaces of the buoys in the contracted position and the inner wall surfaces. The second capture area captures red blood cells after blood is spun in the separation device. The third capture area includes the collection troughs. The third capture area captures platelet rich plasma after blood is spun in the separation device.

The present teachings further provide for a method for separating bone marrow aspirate into different components. The method includes inserting bone marrow aspirate into a rotatable chamber of a bone marrow aspirate separation device having an axis of rotation and an inner wall surface; rotating the chamber for a sufficient period of time such that components of the bone marrow aspirate separate according to density; and stopping rotation of the chamber such that the plurality of buoys move from an expanded position in which the buoys are distal to the axis of rotation to a contracted position in which the buoys are proximal to the axis of rotation to isolate red blood cells of the bone marrow aspirate between the buoys and the inner wall surface, to isolate bone marrow plasma between the buoys and the axis of rotation, and to isolate multipotent cells at a common distance from the axis of rotation as the buoys.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
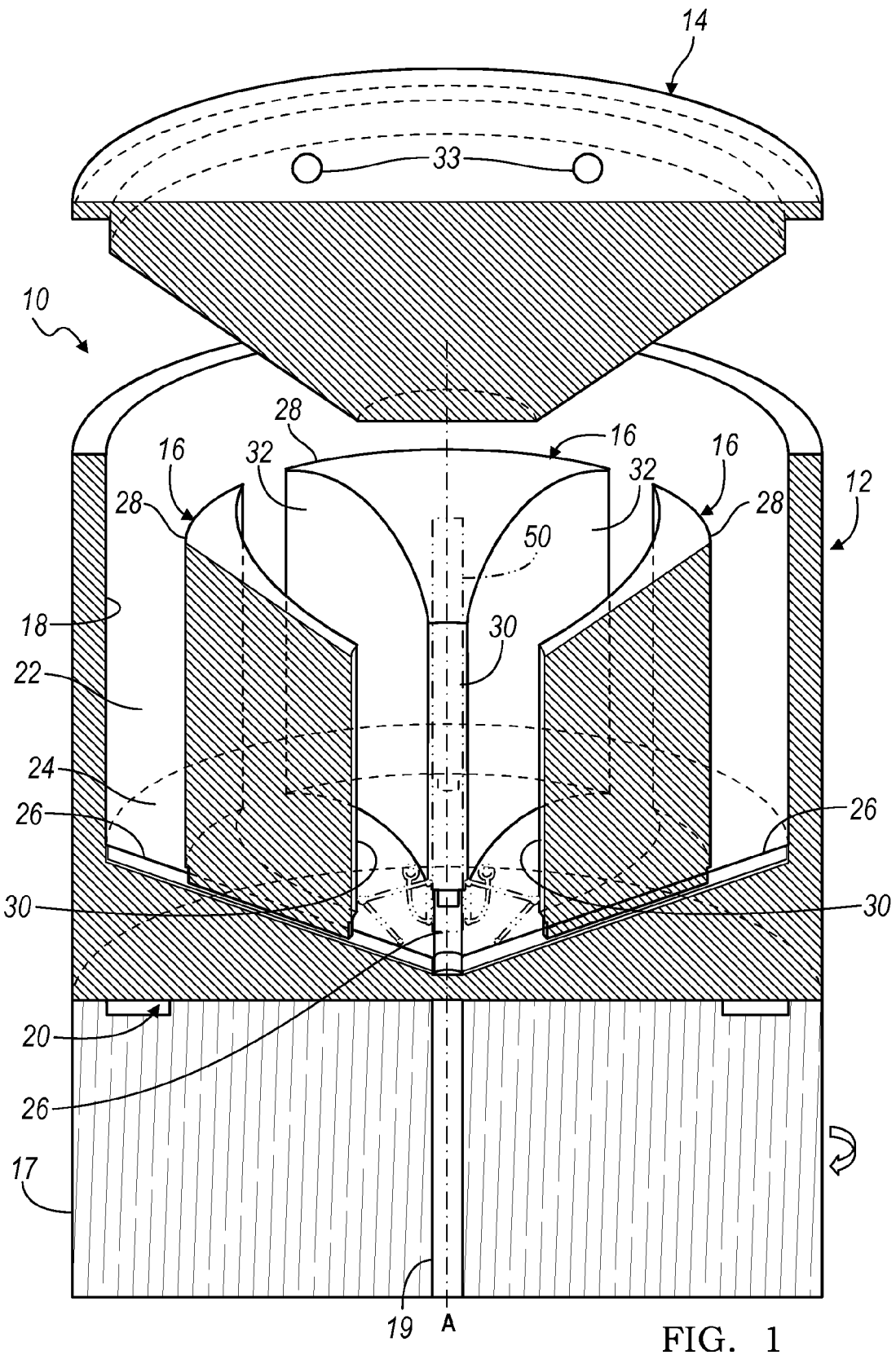
FIG. 1 is sectional side view of a separation device for separating components of a multi-component composition according to the present teachings.
Figure 2A:
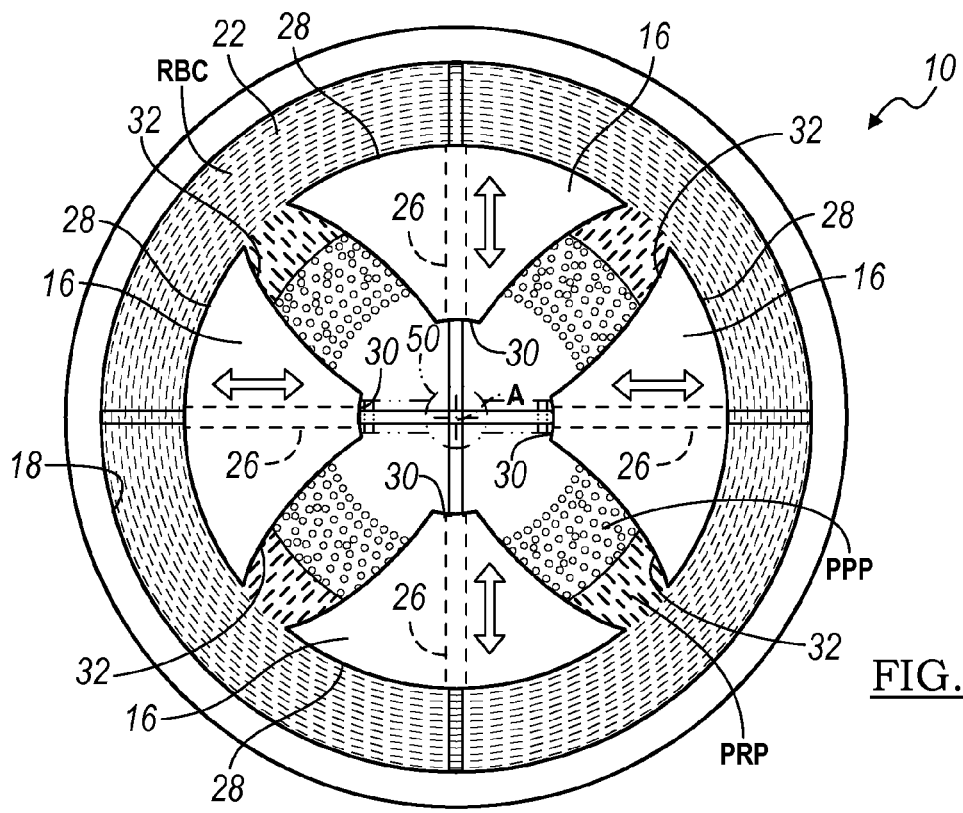
FIG. 2A is a top view of the device of FIG. 1 spinning on a rotating base, the device containing human whole blood.
Figure 2B:
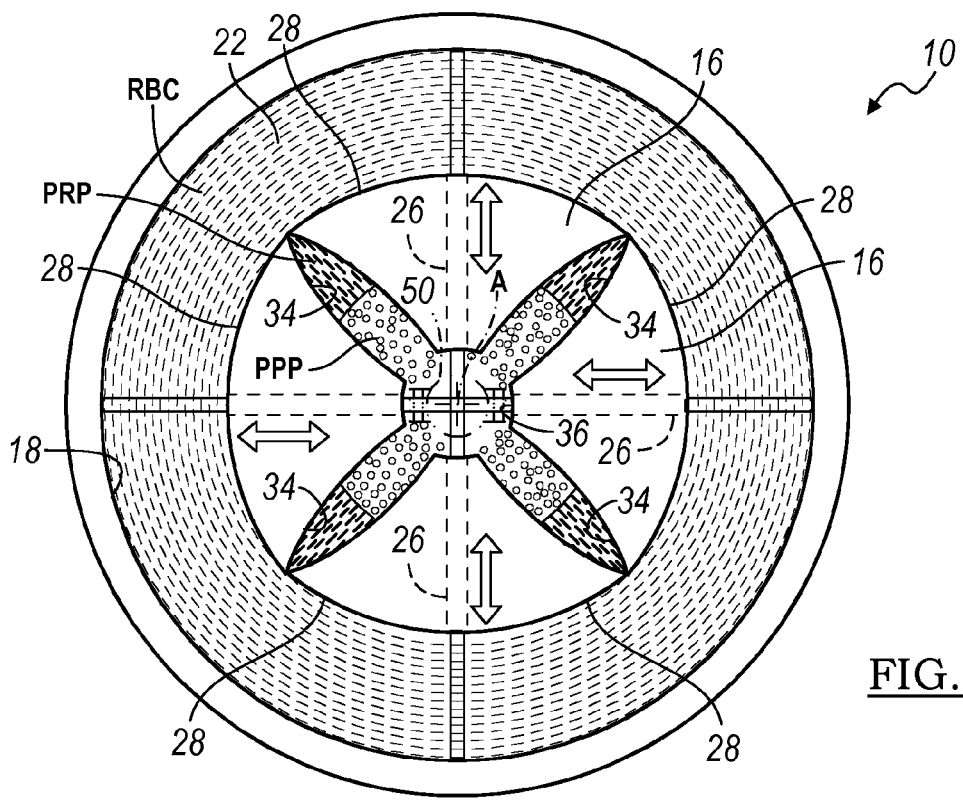
FIG. 2B is a top view of the device of FIG. 1 containing whole blood after it has been spun on a rotating base.

With initial reference to FIGS. 1, 2A, and 2B, a device for separating components of a multi-component composition according to the present teachings is illustrated at reference numeral 10. The device 10 generally includes a housing 12, a cover 14, and a plurality of buoys 16. The device 10 can be rotated or spun using a suitable rotating device 17, such as a Vortech® Base manufactured by Biomet, Inc. of Warsaw, Ind. (model nos. 800-7500A and 800-7600A, for example). The rotating device 17 can include any suitable mechanism for transferring torque from the rotating device 17 to the blood separation device 10, such as a rotating rod or spindle 19. The device 10 can be used to separate components of a variety of different compositions, such as whole blood, blood plasma, mononuclear cells ("MNC"), bone marrow aspirate, spinal fluid, and fat, for example.

The housing 12 includes a cylindrical sidewall 18 and a base 20. The cylindrical sidewall 18 defines a chamber 22. At the center of the chamber 22 is an axis of rotation A that extends longitudinally through the chamber 22. The device 10 rotates about the axis of rotation A when the device 10 is spun on the rotating device 17. The device 10 can include any suitable interface mechanism to permit the device 10 to cooperate with, and be rotated by, the rotating device 17.

The base 20 includes an inclined floor 24. The floor 24 is inclined from the axis of rotation A to the cylindrical sidewall 18. The floor 24 can be inclined at any suitable angle that is less than 90°, such as any suitable angle between about 15° and about 45°, such as about 25°. The floor 24 is inclined at this angle to cause the buoys 16 to move toward the axis of rotation A when the housing 12 is stationary.

The floor 24 includes a plurality of guide tracks 26. The guide tracks 26 extend generally from the axis of rotation A to the cylindrical sidewall 18. The guide tracks 26 can take the form of any suitable device capable of retaining the buoys 16 and permitting the buoys 16 to slide along the inclined floor 24 between the axis of rotation A and the cylindrical sidewall 18. For example, the guide tracks 26 can be rails recessed in, or protruding from, the inclined floor 24.

Each one of the buoys 16 is tapered such that an outer surface 28 of each buoy 16 proximate the cylindrical sidewall 18 has a larger surface area than an inner surface 30, which is proximate the axis of rotation A and distal to the cylindrical sidewall 18. Each buoy 16 includes side surfaces 32 that extend from the ends of the outer surface 28 to the inner surface 30. The outer, inner, and side surfaces 28, 30, and 32 can be of any suitable shape. As illustrated, the outer surfaces 28 are arcuate, the inner surfaces 30 are arcuate, and the side surfaces 32 are arcuate so as to be curved inward or hemispherical. Each buoy 16 is slidably mounted to one of the guide tracks 26 to permit each buoy 16 to slide along the inclined floor 24 and move radially inward and outward between the cylindrical sidewall 18 and the axis of rotation A. The buoys 16 are positioned about the axis of rotation A so as to surround the axis of rotation A.

The buoys 16 are movable between an expanded position (FIGS. 1 and 2A) and a contracted position (FIG. 2B), as further described herein. With additional reference to FIG. 3A, prior to initial rotation of the device 10, the buoys 16 are supported in the expanded position by support arms 38 (for clarity, FIGS. 1, 2A, and 2B do not illustrate the support arms 38). One support arm 38 is provided for each of the buoys 16. Each support arm 38 includes a first end 40 mounted to the inclined floor 24 and a second end 42 mounted to a slidable cylinder 44. The slidable cylinder 44 is mounted to a center post 50 that extends along the axis of rotation A. Between the first end 40 and the second end 42 is a hinged elbow portion 46. Weights 48 are also mounted to the slidable cylinder 44 with a hinge.

Figure 3A:
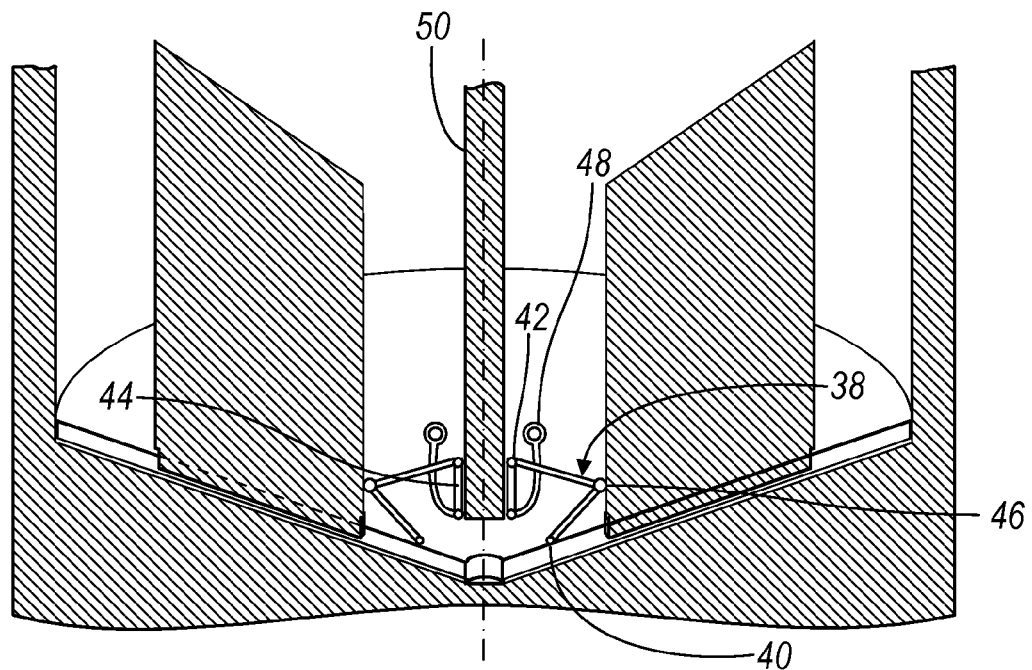
FIG. 3A is an expanded view of support arms of the device of FIG. 1, the support arms in a first position.

Before the housing 12 is initially rotated by the rotating device 17, the elbow portions 46 of the support arms 38 are in an extended position in which they contact the buoys 16 to support the buoys 16 in the expanded position of FIGS. 1, 2A, and 3A. Rotation of the device 10 results in movement of the weights 48 outward from the axis of rotation A towards the cylindrical sidewall 18 and the floor 24 of the chamber 22. As the weights move, the cylinder 44 moves away from the floor 24 along the axis of rotation A and the elbow portions 46 move inward toward the axis of rotation A to permit the buoys 16 to move to the retracted position. The cylinder 44 remains in the raised position of FIG. 3B after rotation of the chamber 22 is stopped, thereby permitting the buoys 16 to settle in the retracted position.

Each buoy 16 can be made of any appropriate material that may have a desired density. For example, when the device 10 is for separating blood, the buoys 16 can generally have a density that permits the buoys 16 to float on RBCS and find interface between RBCS and a PRP buffy coat or MNC fraction. For example, each buoy can have a density of generally between about 1.06 b/cc and about 1.11 g/cc. Further, the buoys 16 can have a density that is approximately equal to, or slightly greater than, the density of platelet rich plasma. To achieve the selected density, the buoys 16 can be formed of a single material or a composite having a plurality of materials. The density of the buoys 16 will also depend on the incline angle of the floor 24 as the angle will affect the position of the buoys 16. The angle of the floor 24 can be any suitable angle between about 15° and about 45°, such as about 25°, such that buoys 16 of a desired density will float on RBCS and find interface between RBCS and the PRP buffy coat or MNC fraction after blood within the device 10 has been spun for a suitable period of time.

The device 10 can be used to separate most any liquid composition into its constituent components by density. With particular reference to FIGS. 2A and 2B, operation of the device 10 to separate RBCs, PPP, and PRP from whole blood is described below.

Whole blood is loaded into the chamber 22 of the device 10 with the buoys 16 held in the expanded position by the elbow portion 46 of the support arms 38, as illustrated in FIGS. 1, 2A, and 3A. When the cover 14 is affixed to the chamber 22, the blood can be loaded through ports 33 in the cover 14. Alternatively, the cover 14 can be removed from the chamber 22 to permit blood to be loaded directly into the chamber 22.

The device 10 is spun using a suitable rotating mechanism, such as a Vortech Base. The device 10 is spun about its axis of rotation A. Rotation of the device 10 causes the hinged elbow portions 46 of the support arms 38 to move toward the axis of rotation A, as described above. However, rotation of the device 10 also causes the buoys 16 to remain in the expanded position even through the elbow portions 46 are no longer in contact with the buoys 16. Further, rotation of the device 10 causes separation of the different components of whole blood according to density.

Thus, as illustrated in FIG. 2A, as the component with the greatest density, RBCs gather at the outermost portion of the chamber 22, between the buoys 16 and the cylindrical sidewall 18. PRP, which is typically present in a buffy coat, gathers between the RBCs and the axis of rotation A in an area between two of the buoys 16. PPP, which is the least dense component, gathers near the axis of rotation A, interior to the RBCs and the PRP. Thus, the PRP gathers between the RBCs and the PPP.

Figure 3B:
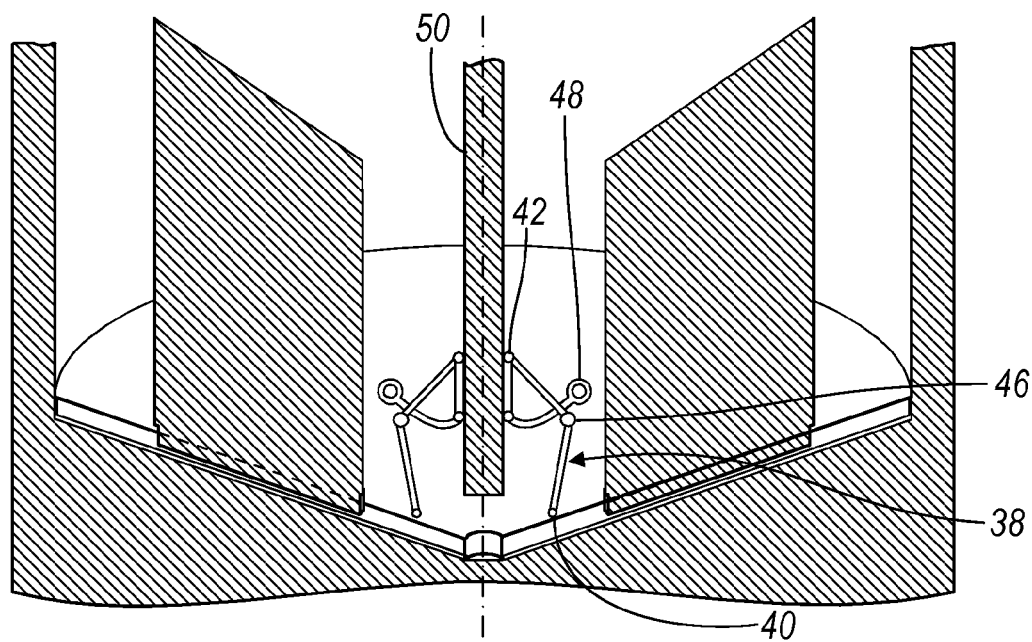
FIG. 3B is an expanded view of support arms of the device of FIG. 1, the support arms in a second position.

As illustrated in FIG. 2B, when the device 10 is stopped from rotating, the buoys 16 slide down the inclined floor 24 along the guide tracks 26 to move radially toward the axis of rotation A until the adjacent buoys 16 contact each other and settle in a contracted position. Movement of the buoys 16 to the contracted position is permitted because, as illustrated in FIG. 3B, the elbow portions 46 disengage the buoys 16 and move toward the axis of rotation A when the device 10 is rotated and remain in this position after the device 10 is stopped from rotating. Further, movement of the buoys 16 is facilitated by the inclined floor 24, which can be angled at from about 15° to about 45°, such as about 25° from the cylindrical sidewall 18 to the axis of rotation A. In the contracted position, adjacent buoys 16 only contact each other at their outer surface 28 to form a cylindrical wall about an exterior of the buoys 16. Because the side surfaces 32 are curved inward, the side surfaces 32 of adjacent buoys 16 do not contact each other. Instead, the side surfaces 32 of adjacent buoys 16 define pockets 34 between the buoys 16 when the buoys 16 are in the contracted position of FIG. 2B.

The majority of the PRP and the PPP is isolated in the pockets 34 after the device 10 is spun for a suitable period of time. The PRP is isolated at an outer portion of each pocket 34, proximate to the cylindrical sidewall 18. The PPP is isolated at an inner portion of each pocket 34, proximate the axis of rotation A. At least some of the isolated PPP can also gather in an interior chamber 36 formed between the buoys 16 at the axis of rotation and proximately surrounding the axis of rotation A. The interior chamber 36 is partially defined by the inner surface 30 of each buoy 16 and has a generally cylindrical shape. The majority of the RBCS are isolated between the contracted buoys 16 and the cylindrical sidewall 18.

The isolated RBCs, PRP, and PPP can be extracted from the device in any suitable manner using any suitable device. For example, the cover 14 can be removed and a select amount of RBCs, PRP, and/or PPP can be extracted using a syringe. The extracted RBCs, PRP, and/or PPP can be used for any suitable biological application.

Figure 4:
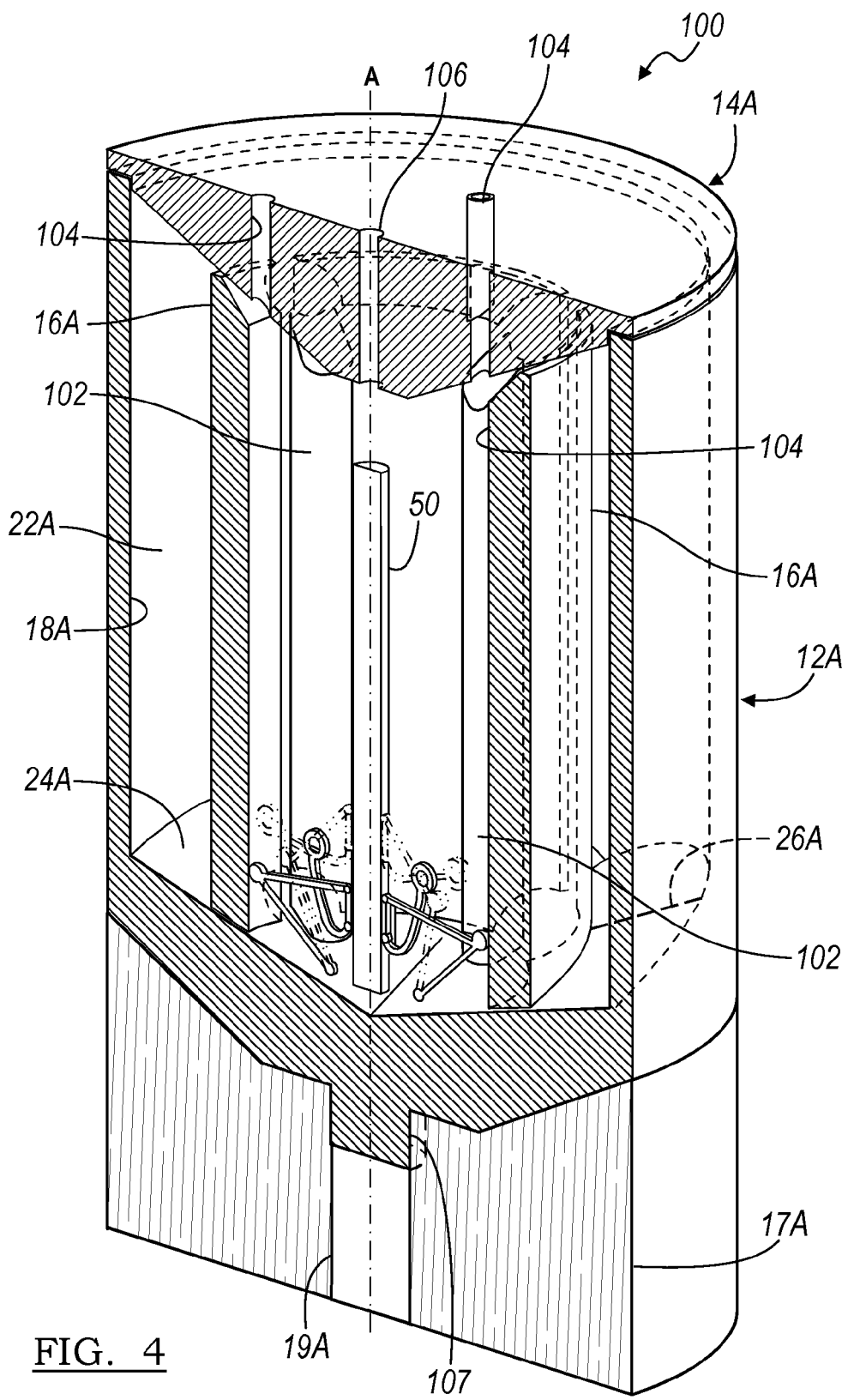
FIG. 4 is a sectional side view of a another blood separation device according to the present teachings.
Figure 5A:
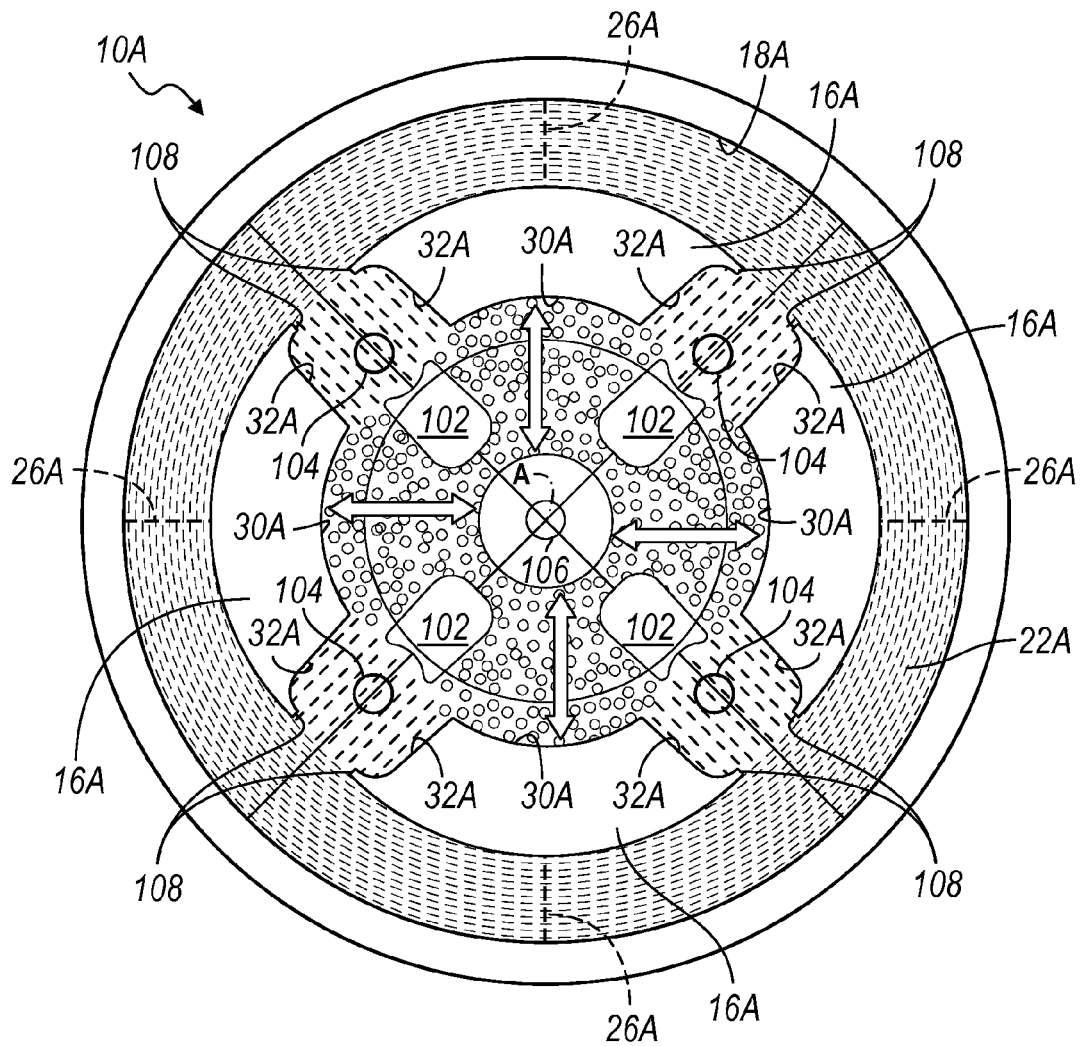
FIG. 5A is a top view of the device of FIG. 4 spinning on a rotating base, the device containing human whole blood.
Figure 5B:
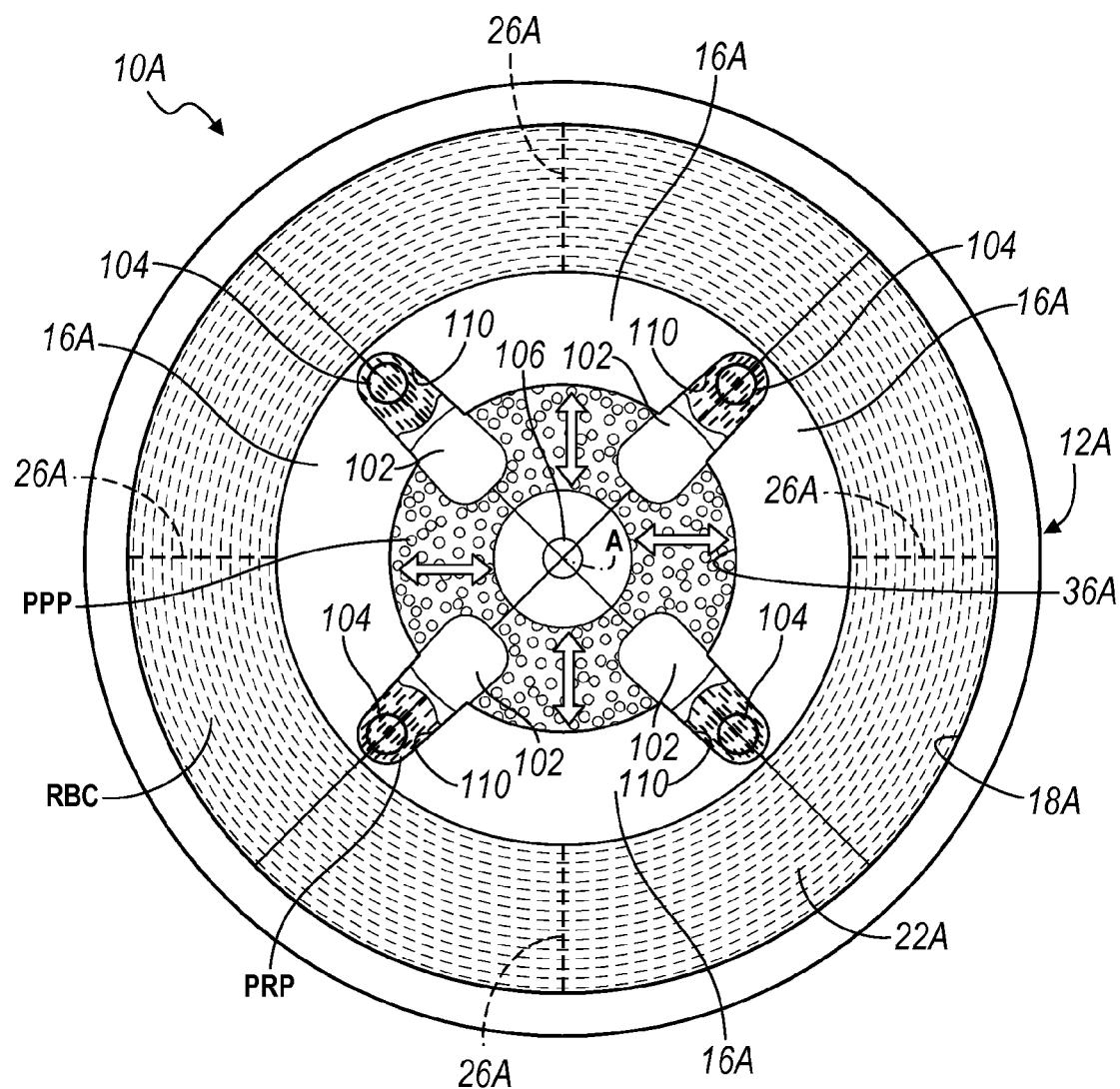
FIG. 5B is a top view of the device of FIG. 4 containing whole blood after it has been spun on a rotating base.
Figure 6:
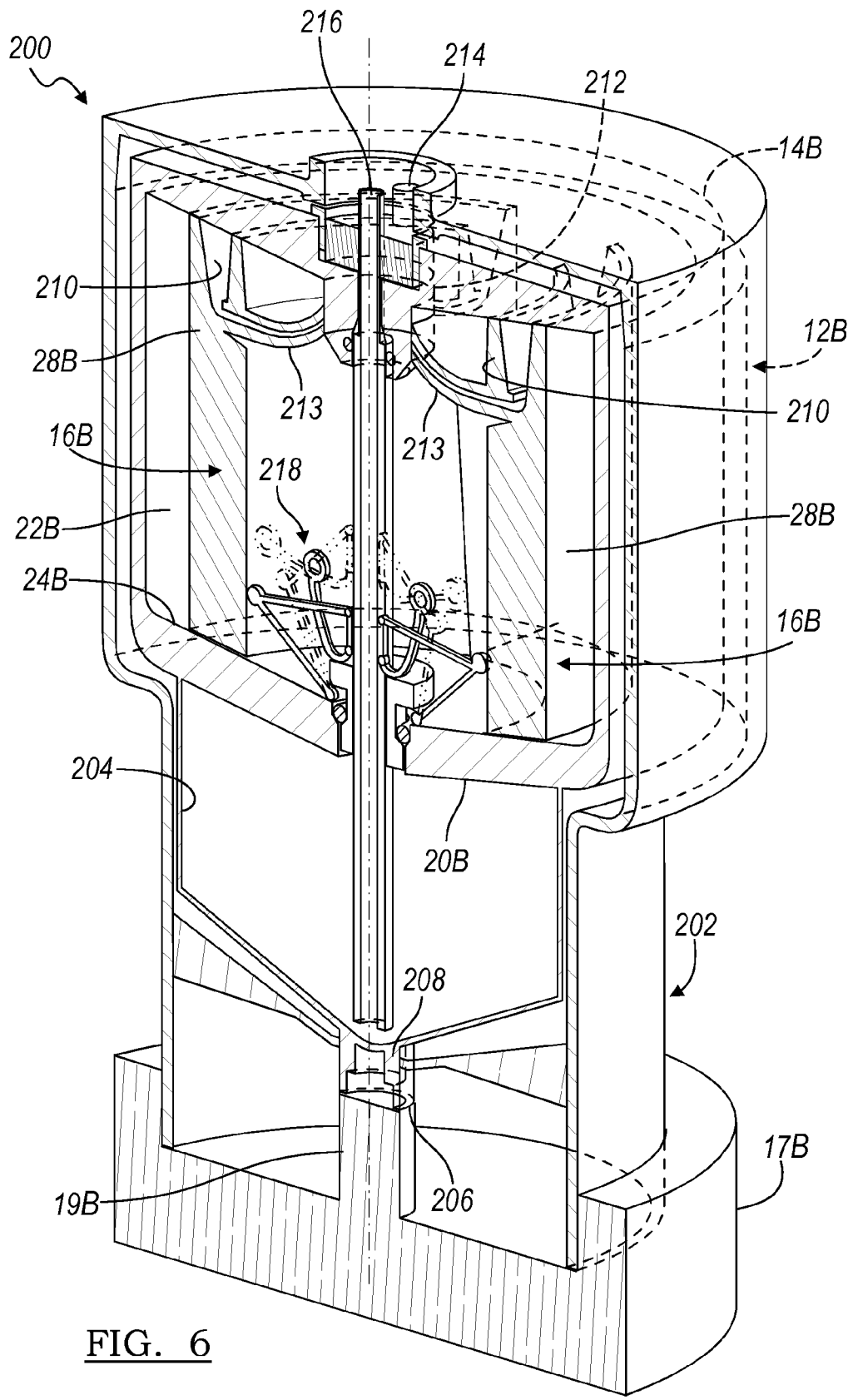
FIG. 6 is a sectional side view of another blood separation device according to the present teachings.

With reference to FIGS. 4, 5A, and 5B, a blood separation device 100 is illustrated. Features of the blood separation device 100 that are similar to the features of the blood separation device 10 are illustrated with like reference numbers, but also including the letter "A." With respect to these similar features, the above description of the device 10 also applies to the device 100.

The device 100 further includes stop posts 102, PRP withdrawal ports 104, PPP withdrawal ports 106, and an interface 107 for cooperating with a suitable rotational device, such as a Vortech Base (model numbers 800-7500A and 800-7600A) manufactured by Biomet Biologics of Warsaw, Ind.

The posts 102 are positioned about the axis of rotation A between the buoys 16A. The posts 102 generally extend from the inclined floor 24A to an upper surface of the cylindrical sidewall 18A, proximate to the cover 14A when it is in place over the chamber 22A. The buoys 16A include side tabs 108 that extend from the side surfaces 32A of the buoys 16A. The side surfaces 32A are generally planar. As illustrated in FIG. 5B, in the contracted position the side tabs 108 of adjacent buoys 16A contact each other and a portion of the side surfaces 32A opposite to the side tabs 108 contacts the posts 102 to form a pocket 110 between adjacent buoys 16A and the posts 102. After whole blood is spun for a suitable period of time and the buoys 16 have moved to the contacted position (FIG. 5B) from the expanded position (FIG. 5A) after rotation of the device 10, PRP is isolated in the pockets 110, isolated PPP gathers in the interior chamber 36A, and isolated RBCS gather between the buoys 16A and the cylindrical sidewall 18A.

The PRP withdrawal ports 104 are elongated tubes through which PRP can flow. The PRP withdrawal ports 104 are located in the pockets 110. The PRP withdrawal ports 104 have a distal end proximate to the inclined floor 24 and a proximal end that mates with the cover 14A when the cover 14A is in place over the chamber 22A. The PRP withdrawal port 104 extends through the cover 14. The PRP can be withdrawn through the ports 104 using any suitable extraction device, such as a syringe.

The PPP withdrawal port 106 is located within the interior chamber 36A, at or proximate to the axis of rotation A. The PPP withdrawal port 106 has a distal end proximate to the inclined floor 24 and a proximal end that mates with the cover 14A when the cover 14A is in place over the chamber 22A. The PPP withdrawal port 106 extends through the cover 14. The PPP can be withdrawn through the port 106 using any suitable extraction device, such as a syringe.

With reference to FIGS. 6, 7A, 7B, 8A, and 8B a blood separation device 200 is illustrated. Features of the blood separation device 200 that are similar to the features of the blood separation device 10 are illustrated with like reference numbers, but also including the letter "B". With respect to these similar features, the above description of the device 10 also applies to the device 200.

The device 200 further includes a casing 202 and a collection basin 204. The casing 202 surrounds the housing 12B and the collection basin 204. The casing 202 includes an interface 206 that can rotationally receive the collection basin 204 and a rotating device, such as the rotating rod 19B of the rotating device 17B. The interface 206 can transfer rotational torque generated by the rotating device to the collection basin 204 and the chamber 22B. The collection basin 204 extends from the base 20B of the device 200. The collection basin 204 includes a fitting 208 that is rotationally received within the interface 206.

The device 200 further includes PRP collection troughs 210. The troughs 210 are open at the sidewalls 32B, which are generally planar. The troughs 210 are present in the buoys 16B at an upper surface of each buoy 16B. The troughs 210 are in fluid communication with a central PRP collection bowl 212. The collection bowl 212 is located at a central portion of the chamber 22B at the axis of rotation A. The troughs 210 are in fluid communication with the collection bowl 212 by way of fluid lines 213 that extend between each trough 210 and the collection bowl 212. A PRP outlet port 214 extends from the collection bowl 212 to an exterior of the device through the cover 14B and through the casing 202.

The device 200 includes a PPP withdrawal port 216. The PPP withdrawal port 216 extends along the axis of rotation A. The withdrawal port 216 includes a distal end located in the collection basin 204 and proximal end that protrudes from the housing 12 and extends through the cover 14B and the casing 202.

Figure 8A:
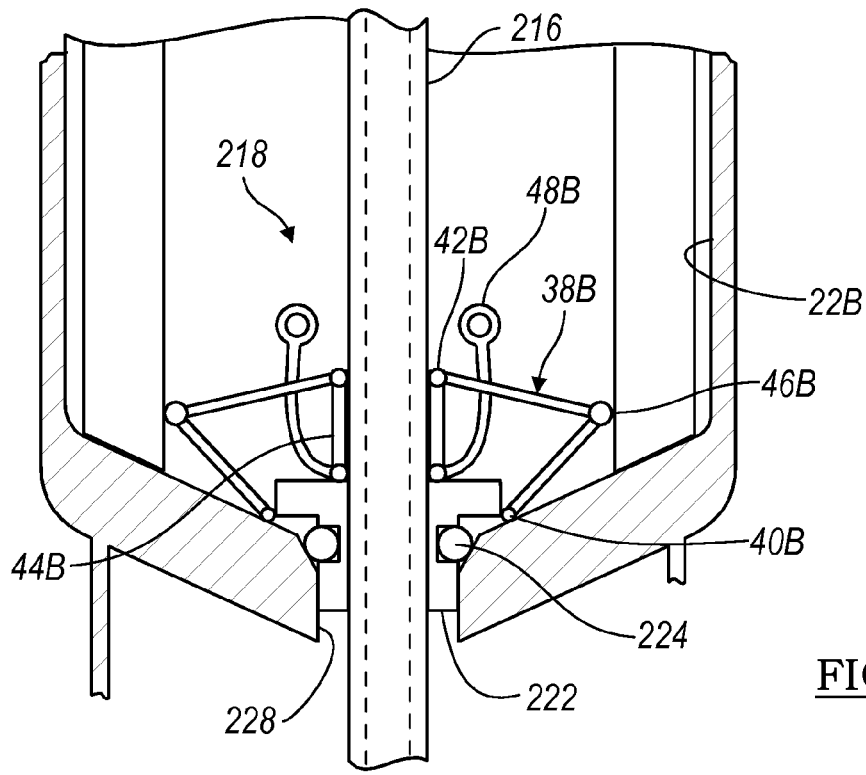
FIG. 8A is an expanded view of a valve of the device of FIG. 6, the device in a stationary position and the valve in a lowered position.
Figure 8B:
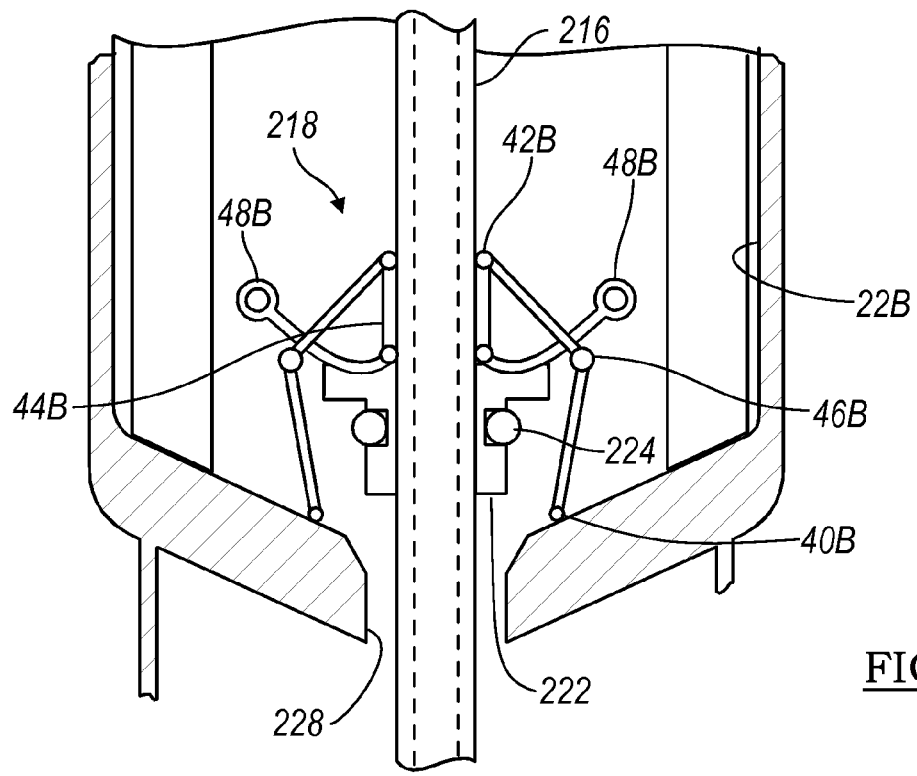
FIG. 8B is an expanded view of the valve of FIG. 6, the device in a rotating position and the valve in a raised position.

With additional reference to FIGS. 8A and 8B, the device 200 includes a valve 218. The valve 218 can be any suitable valve, such as the valve described in U.S. Patent Publication No. 2006/0175244 assigned to Hanuman LLC and Cell Factor Technologies, Inc. (filed Jan. 30, 2006; application Ser. No. 11/342,749), which is hereby incorporated by reference. The valve 218 includes a plug 222. The plug 222 is mounted to the cylinder 44B. The plug 222 includes a seal 224 that extends around an exterior of the plug 222. The seal 224 can be any suitable device or material that prevents the passage of materials. Also mounted to the cylinder 44B are the support arms 38B.

The plug 222 and the cylinder 44B are slidably mounted to the PPP port 216 at the axis of rotation A. The plug 222 is mounted such that it extends around the PPP port 216 and can slide up and down along the PPP port 216 between a lowered position (FIG. 8A) and a raised position (FIG. 8B). In the lowered position, the plug 222 is seated within an opening 228 of the inclined floor 24B, which surrounds the PPP port 216. In the raised position, the weights 48B extend outward toward the cylindrical sidewall 18B to raise the plug 222 out from within the opening to permit the passage of materials from the chamber 22B to the collection basin 204.

Figure 7A:
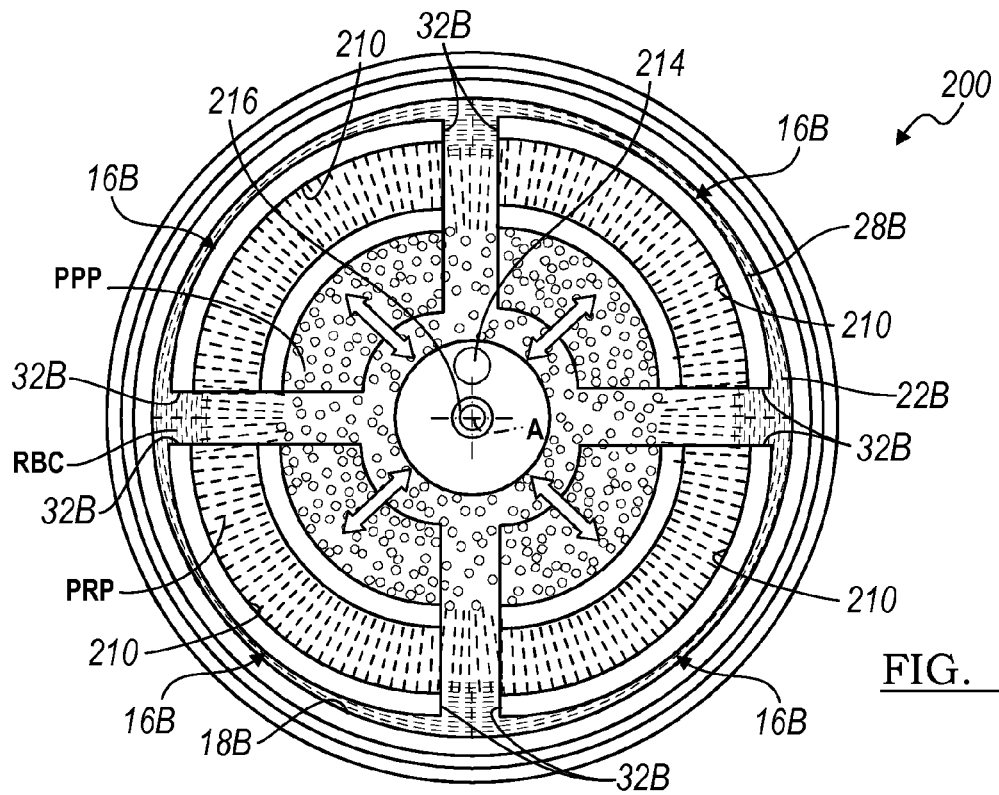
FIG. 7A is a top view of the device of FIG. 6 spinning on a rotating base, the device containing human whole blood.

In operation, a suitable rotating device, such as the rotating device 17A, is connected to the interface 206 to rotate the device 200 and the collection basin 204. As illustrated in FIG. 7A, rotating the device causes the components of whole blood to separate by density such that the RBCS are isolated between the cylindrical sidewall 18B and the buoys 16B, PRP is isolated in the collection troughs 210 of the buoys 16B, and PPP is isolated in the interior chamber 36B between the buoys 16B and the axis of rotation A. Rotating the device 200 further causes the plug 222 to move from the lowered position of FIG. 8A to the raised position of FIG. 8B and out from within the opening 228 to permit PPP within the interior chamber 36B to pass through the opening 228 into the collection basin 204.

Figure 7B:
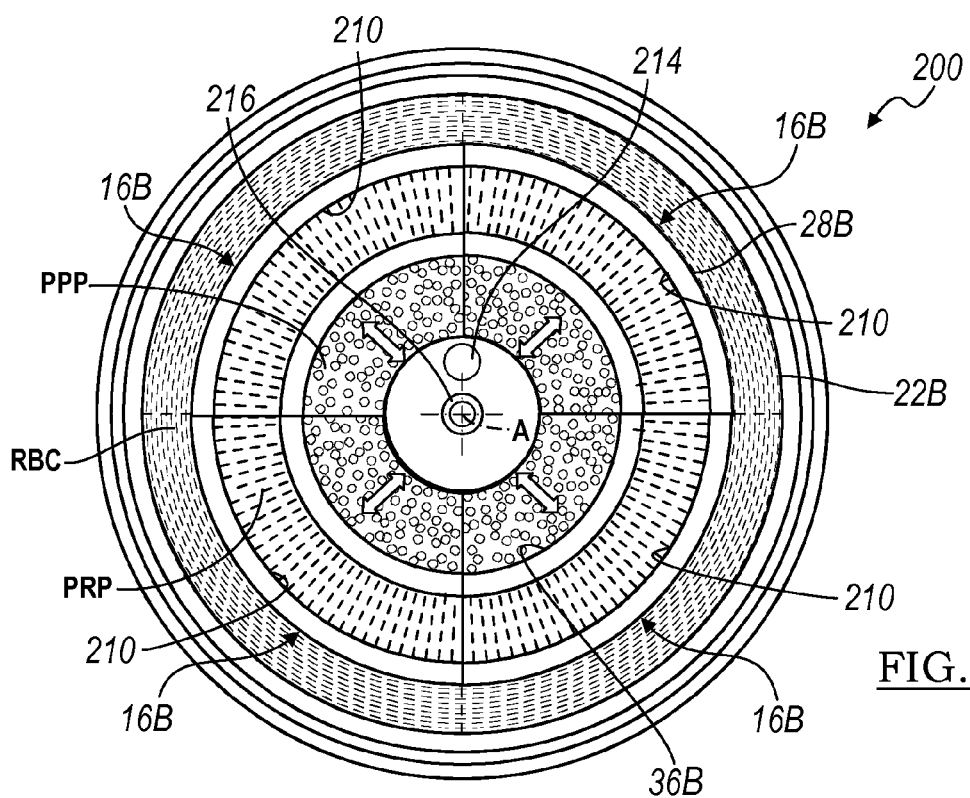
FIG. 7B is a top view of the device of FIG. 6 containing whole blood after it has been spun on a rotating base.

After the device 200 is spun, the buoys 16B move radially toward the axis of rotation A to isolate the PPP at the interior chamber 36B, the PRP in the collection troughs 210, and the RBCS between the outer surfaces 28B of the buoys 16B and the cylindrical sidewall 18B, as illustrated in FIG. 7B. The PRP can be removed via the PRP outlet port 214 using a suitable extraction device, such as a syringe. Using a syringe connected to the outlet port 214, PRP can be extracted from within the collection trough 210 by way of the fluid lines 213. PPP can be extracted from within the basin 204 by way of the PPP withdrawal port 216 using a suitable extraction device, such as a syringe. To facilitate removal of water from the PPP, dessicating beads can be provided within the collection basin 204.

Each device 10, 100, and 200 can also be used to separate components of bone marrow aspirate. For example, bone marrow aspirate can be obtained using any suitable bone marrow aspiration needle. To obtain bone marrow aspirate for separation, the bone marrow aspiration needle is advanced into the bone cortex and ultimately into the bone marrow cavity from where the bone marrow aspirate is withdrawn, typically using a syringe connected to the bone marrow aspiration needle. Any suitable amount of bone marrow aspirate can be used, such as about 300 cc, about 60 cc, or less than 60 cc. A suitable anticoagulant in a suitable amount is added to the bone marrow aspirate after it has been withdrawn from the bone marrow cavity.

When using the device 10 to isolate multipotent cells from bone marrow aspirate, the buoys 16 are set to a density that is approximate to, or slightly greater than, the density of the multipotent cells. This will allow the multipotent cells to be captured in the pockets 34. For example, the density of the buoys 16 can be about 1.08 g/cc to about 1.11 g/cc.

When using the device 10 to separate the components of bone marrow aspirate, the bone marrow aspirate is loaded into the chamber device 10 in the same manner that blood is. The device is then rotated according to the above description for separating blood components. After rotation and after the buoys move to the contracted position, the bone marrow aspirate is separated such that bone marrow plasma is isolated in a first capture area between the inner surface of the buoys 30 and the axis of rotation A. The heavy components of the bone marrow aspirate, such as the RBCS, are isolated in a second capture area between the cylindrical sidewall 18 and the outer surface 28 of the buoys 16. The multipotent cells are isolated in a third capture area that includes the pockets 34. The third capture area is between the first capture area and the second capture area. The different components of bone marrow aspirate can be removed in the same manner described above with respect to the different blood components.

While only the device 200 is illustrated as having the collection basin 204, the devices 10 and 100 can also include the collection basin 204 and the valve 218. Further, while only the device 100 is illustrated as including the ports 104 and 106, the ports 104 and 106 can be included in the device 10.

While devices 10, 100, and 200 each include four buoys 16, each device can include any suitable number of buoys 16. For example, the devices 10, 100, and 200 can include more than four buoys 16 and as few as one, two, or three buoys 16. Regardless of the number of buoys 16 provided, the buoys 16 can generally move radially along the inclined floor 24 between a contracted position in which the buoys 16 are proximate to the axis of rotation A and an expanded position in which the buoys 16 are distal to the axis of rotation A.

The devices 10, 100, and 200 can be used to isolate most any liquid composition into its constituent components by density. In order to adapt the devices 10, 100, and 200 to be used to separate different fluids, the density of the buoys 16 can be modified to approximate, or be slightly greater than, the density of the particular fluid component to be isolated, such that the buoys 16 will float on or find equilibrium in the rotating chamber 22 with the component to be isolated.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A device for separating components of a composition according to density comprising:
    a rotatable chamber having an axis of rotation; and
    a plurality of buoys positioned within said rotatable chamber and about the axis of rotation and radially movable between an expanded position in which said buoys are at a first location relative to said axis of rotation and a contracted position in which said buoys are at a second location relative to said axis of rotation, said first location is further from said axis of rotation than said second location, said buoys are movable in response to force generated during rotation of said rotatable chamber.

2. The device of claim 1, wherein said composition includes one of the following: whole blood, blood plasma, mononuclear cells, bone marrow aspirate, spinal fluid, and fat.

3. The device of claim 1, wherein said rotatable chamber includes a floor that is inclined from said axis of rotation to a sidewall of said chamber.

4. The device of claim 3, wherein said floor is inclined at an angle of about 15 degrees to about 45 degrees.

5. The device of claim 1, wherein said buoys have a density of about 1.06 g/cc to about 1.11 g/cc.

6. The device of claim 1, wherein said buoys define a first capture area between an inner surface of said buoys and the axis of rotation, a second capture area between an outer surface of said buoys and a cylindrical sidewall of said chamber, and a third capture area between said first capture area and said second capture area.

7. The device of claim 1, wherein said buoys isolate the following: platelet poor plasma at a first position proximate to said axis of rotation; red blood cells at a second position distal to said axis of rotation; and platelet rich plasma, buffy coat, or cell rich fractions at a third position that is between said first position and said second position.

8. The device of claim 1, wherein said buoys each include an arcuate inner surface, an arcuate outer surface, and hemispherical side surfaces; and
    wherein said buoys define, when in said contracted position, a first capture area between said arcuate inner surfaces and the axis of rotation, a second capture area between said arcuate outer surfaces and a cylindrical sidewall of said rotatable chamber, and a third capture area between said hemispherical side surfaces of neighboring buoys.

9. The device of claim 1, wherein said buoys each include an arcuate inner surface, an arcuate outer surface, substantially linear side surfaces, and side tabs extending from each of said side surfaces; and
    wherein said buoys define, when in said contracted position, a first capture area between said arcuate inner surfaces and the axis of rotation, a second capture area between said arcuate outer surfaces and a cylindrical sidewall of said rotatable chamber, and a third capture area between said side surfaces that is partially defined by said side tabs of neighboring buoys.

10. The device of claim 1, wherein said buoys each include an arcuate inner surface, an arcuate outer surface, and a trough between said arcuate inner surface and said arcuate outer surface; and
    wherein said buoys define, when in said contracted position, a first capture area between said arcuate inner surfaces and the axis of rotation, a second capture area between said arcuate outer surfaces and a cylindrical sidewall of said rotatable chamber, and a third capture area defined by said troughs.

11. The device of claim 1, wherein said plurality of buoys include a trough connected to a collection bowl at said axis of rotation with a fluid line.

12. The device of claim 1, further comprising a collection basin attached to a base of said rotatable chamber.

13. The device of claim 12, further comprising a valve positioned to regulate passage of material between said rotatable chamber and said collection basin.

14. A blood component separation device comprising:
    a rotatable chamber having an axis of rotation, an inner wall surface, and a floor that is inclined from said axis of rotation to said inner wall surface;
    a plurality of buoys surrounding the axis of rotation and slidable along said floor so as to move radially between an expanded position in which said buoys are distal to the axis of rotation when said chamber is rotating and a contracted position in which said buoys are proximate to the axis of rotation when said chamber is stationary, said buoys have a density that is proximate to the density of platelet rich plasma;
    a first capture area between an inner surface of said buoys in the contracted position and the axis of rotation, said first capture area captures platelet poor plasma after blood is spun in said separation device;
    a second capture area between an outer surface of said buoys in the contracted position and the inner wall surface of the rotatable chamber, said second capture area captures red blood cells after blood is spun in said separation device; and
    a third capture area between said first capture area and said second capture area, said third capture area captures platelet rich plasma after blood is spun in said separation device.

15. The separation device of claim 14, wherein said buoys have a density of about 1.06 g/cc to about 1.11 g/cc.

16. The separation device of claim 14, wherein said inner surface is arcuate, said outer surface is arcuate, and said sidewalls are hemispherical.

17. The separation device of claim 14, further comprising side tabs extending from each of said side sidewalls, said side tabs partially define said third capture area;
    wherein said inner surface is arcuate, said outer surface is arcuate, and said sidewalls are substantially linear.

18. The separation device of claim 14, wherein said buoys further comprise a trough between said inner surface and said outer surface; and
    wherein said third capture area includes said trough.

19. The separation device of claim 18, wherein said trough is connected to a collection bowl at the axis of rotation with a fluid line.

20. The separation device of claim 14, further comprising a collection basin attached to a base of said rotatable chamber.

21. The separation device of claim 20, further comprising a valve positioned to regulate passage of material between said rotatable chamber and said collection basin.

22. A blood component separation device comprising:
- a rotatable chamber having an axis of rotation, an inner wall surface, and a floor that is inclined from said axis of rotation to said inner wall surface;
- a plurality of buoys positioned within said rotatable chamber and surrounding the axis of rotation, each of said buoys having a density that permits said buoys to settle at an interface between red blood cells and a platelet rich plasma buffy coat, each of said buoys slidable along said floor so as to move radially between an expanded position in which said buoys are distal to said axis of rotation when said chamber is rotating and a contracted position in which said buoys are proximate to said axis of rotation when said chamber is stationary and, each of said buoys including:
  - an arcuate outer surface;
  - an arcuate inner surface;
  - a substantially linear side surface; and
  - a collection trough between said outer surface and said inner surface;
- a collection bowl at the axis of rotation;
- a fluid line extending between said collection trough and said collection bowl;
- a collection basin attached to a base of said rotatable chamber;
- a valve positioned to regulate passage of material between said rotatable chamber and said collection basin;
- a first capture area between said inner surfaces of said buoys in the contracted position and the axis of rotation, said first capture area captures platelet poor plasma after blood is spun in said separation device;
- a second capture area between said outer surfaces of said buoys in the contracted position and said inner wall surfaces, said second capture area captures red blood cells after blood is spun in said separation device; and
- a third capture area including said collection troughs, said third capture area captures platelet rich plasma after blood is spun in said separation device.

* * * * *

UNITED STATES PATENT AND TRADEMARK OFFICE
CERTIFICATE OF CORRECTION

PATENT NO. : 8,142,342 B2
APPLICATION NO. : 13/223751
DATED : March 27, 2012
INVENTOR(S) : Jacy C. Hoeppner It is certified that error appears in the above-identified patent and that said Letters Patent is hereby corrected as shown below:

IN THE SPECIFICATIONS:

Column 1, Line 24, "(RBCS)" should be --(RBCs)--.
Column 2, Line 13, "red flood cells" should be --red blood cells--.
Column 3, Line 12, After "is" insert --a--.
Column 4, Line 65, "RBCS" should be --RBCs--.
Column 4, Line 66, "RBCS" should be --RBCs--.
Column 5, Line 10, "RBCS" should be --RBCs--.
Column 5, Line 11, "RBCS" should be --RBCs--.
Column 5, Line 32, "through" should be --though--.
Column 6, Line 8, "RBCS" should be --RBCs--.
Column 6, Line 43, "RBCS" should be --RBCs--.
Column 7, Line 61, "RBCS" should be --RBCs--.
Column 8, Line 7, "RBCS" should be --RBCs--.
Column 8, Line 46, "RBCS" should be --RBCs--.

Signed and Sealed this
Third Day of July, 2012

David J. Kappos
*Director of the United States Patent and Trademark Office*